United States Patent [19]

Bunker

[11] Patent Number: 4,540,722

[45] Date of Patent: Sep. 10, 1985

[54] DENTIN AND ENAMEL ADHESIVE

[75] Inventor: James E. Bunker, White Bear Lake, Minn.

[73] Assignee: Minnesota Mining and Manufacturing Company, St. Paul, Minn.

[21] Appl. No.: 339,290

[22] Filed: Jan. 15, 1982

[51] Int. Cl.³ .......................................... C08F 130/02
[52] U.S. Cl. ................................. 523/109; 433/199.1; 526/266; 526/274; 526/277; 526/278
[58] Field of Search ............... 526/266, 274, 277, 278; 523/109

[56] References Cited

U.S. PATENT DOCUMENTS

| | | | |
|---|---|---|---|
| 2,856,390 | 10/1958 | Coover et al. | 526/276 |
| 4,182,035 | 1/1980 | Yamauchi et al. | 433/228 |
| 4,222,780 | 9/1980 | Shibantani et al. | 106/35 |
| 4,235,633 | 11/1980 | Tomioka et al. | 106/35 |
| 4,251,565 | 2/1981 | Bowen | 427/2 |
| 4,259,075 | 3/1981 | Yamauchi et al. | 433/217 |
| 4,259,117 | 3/1981 | Yamauchi et al. | 526/277 |

FOREIGN PATENT DOCUMENTS 2711234  9/1977  Fed. Rep. of Germany.
2818068  11/1978  Fed. Rep. of Germany.

OTHER PUBLICATIONS

Jedrychowski, J. R., Caputo, A. A., and Prola, J., "Influence of a Ferric Chloride Mordant Solution on Resin—Dentin Retention", *J. Dent. Res.*, 60, 2, 134–138 (1981).
Hendrickson, et al., *Organic Chemistry*, Third Edition, pp. 796–799, (McGraw Hill Co., 1970).
Bowen, R. L., "Adhesive Bonding of Various Materials to Hard Tooth Tissues. VII. Metal Salts as Mordants for Coupling Agents", *Dental Adhesive Materials*, Proceedings from a Symposium held Nov. 8–9, 1973, Moskowitz, H. D., Ward, G. T. and Woolridge, E. D., Eds. pp. 205–221 (1974).
Bowen, R. L., "Adhesive Bonding of Various Materials to Hard Tooth Tissues. XIV. Enamel Mordant Selection Assisted by ESCA (XPS)", *J. Dent. Res.*, 57, 4, 551–556 (1978).
Bowen, R. L., McClendon, L. T., and Gills, T. E., "Adhesive Bonding of Various Materials to Hard Tooth Tissues. XV. Neutron Activation Analysis of Dentin Sorption of Mordant Salts", *J. Dent. Res.*, 57, 2, 255–260 (1978).
Chem. Ab. No. 90:192576v for Japanese Laid-Open Application No. 78-138441.
Chem. Ab. No. 90:210171r for Japanese Laid-Open Application No. 78-21438.
Chem. Ab. No. 90:210175v for Japanese Laid-Open Application No. 78-28339.
Chem. Ab. No. 90:110006x and Suggested Translation of Claims for Japanese Laid-Open Application No. 78-113843.
Chem. Ab. No. 90:110007y and 90:127574d for Japanese Laid-Open Application No. 78-134037.
Chem. Ab. No. 90:157097t for Japanese Laid-Open Application No. 78-144939.
Chem. Ab. No. 88:7867p and Suggested Translation of Claims for Japanese Laid-Open Application No. 77-113089.
Suggested Translation of Claims for Japanese Laid-Open Application No. 78-30193.
Chem. Ab. No. 89:65283b for Japanese Laid-Open Application No. 78-39331.

*Primary Examiner*—Harry Wong, Jr.
*Attorney, Agent, or Firm*—Donald M. Sell; James A. Smith; David R. Cleveland

[57] ABSTRACT

Dental liner and primer compositions having improved adhesion to dentin and containing a metal dissolved in a polar organic solvent, said metal being selected from Fe, Cu, Mn, Co, Sn, Cr, Ni, and Zn.

24 Claims, No Drawings

DENTIN AND ENAMEL ADHESIVE

TECHNICAL FIELD

This invention relates to the field of polymerizable compositions. In addition, this invention relates to compositions for use as liners to which are applied restoratives and composites useful for the repair of teeth, and to compositions for use as primers to which are applied adhesives useful in fastening orthodontic brackets or crowns to teeth. This invention also relates to a method for repairing, adhering, or altering the position of teeth, through the use of such compositions as liners or primers.

BACKGROUND ART

Practitioners in the field of dentistry have long sought polymerizable compositions which would adhere well to dentin (and to tooth structure in general), and some commercially available polymerizable compositions have been utilized as dentin adhesives.

For example, there has been introduced in Japan a dental liner composition, under the name "Clearfil Bond System F" (hereinafter, "Clearfil"), utilizing a two-part resin system. The first (catalyst) portion of such resin system contains a polymerizable phosphoric acid of unreported structure, but believed to be

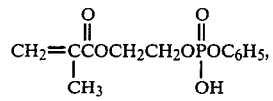

and about 2 weight percent benzoyl peroxide. The second (accelerator) part of such resin system contains an ethanolic solution containing about 3 weight percent sodium benzene sulfinate and about 1 weight percent N,N-dihydroxyethyl-p-toluidine (the latter compound will be referred to hereafter as "DHPT").

My copending U.S. patent application Ser. No. 234,560, filed Feb. 13, 1981, now U.S. Pat. No. 4,482,505 describes polymerizable compositions which adhere well to dentin and enamel. These compositions contain an organic ester of one or more acids of phosphorus, said ester having chlorine or bromine bonded directly to phosphorus, and the organic radical of said ester containing at least one polymerizable functional group.

R. L. Bowen has described another means for obtaining adhesion to dentin, through the use of a multiple step procedure. In a first step of such procedure, a "mordant" prewash solution containing a cation having greater electronegativity than calcium (e.g., $Fe^{+3}$, $Cu^{+2}$, $Al^{+3}$, $Zn^{+2}$, or $Co^{+2}$) is applied to a treatment site of a tooth. In a second step, a "polyfunctional surface-active comonomer", or "polySAC", is applied to the prewash-treated tooth surface. Next, a dental resin or composite material is applied to the polySAC-treated tooth surface and allowed to harden, see U.S. Pat. No. 4,251,565, Bowen, R. L., "Adhesive Bonding of Various Materials to Hard Tooth Tissues. VII. Metal Salts as Mordants for Coupling Agents", *Dental Adhesive Materials*, Proceedings from a Symposium held Nov. 8–9, 1973, Moskowitz, H. D., Ward, G. T., and Woolridge, E. D., Eds., pp. 205–221 (1974), Bowen, R. L., "Adhesive Bonding of Various Materials to Hard Tooth Tissues. XIV. Enamel Mordant Selection Assisted by ESCA (XPS)", *J. Dent. Res.*, 57, 4, 551–556 (1978), and Bowen, R. L., McClendon, L. T., and Gills, T. E., "Adhesive Bonding of Various Materials to Hard Tooth Tissues. XV. Neutron Activation Analysis of Dentin Sorption of Mordant Salts", *J. Dent. Res.*, 57, 2, 255–260 (1978). Additional information concerning the effect of mordant solutions (using ferric chloride as the mordant species) is contained in Jedrychowski, J. R., Caputo, A. A. and Prola, J., "Influence of a Ferric Chloride Mordant Solution on Resin-dentin Retention", *J. Dent. Res.*, 60, 2, 134–138 (1981).

DISCLOSURE OF INVENTION

The above-described mordant prewash technique requires that the dentist employ a separate prewash step prior to application of a dental liner or primer composition to the treatment site. It would be desirable to eliminate this prewash step. The present invention provides, in one aspect, dental liner or primer compositions (hereafter sometimes referred to collectively as "dental bonding compositions") comprising a mixture of:

(a) polymerizable phosphorus compound,
(b) an effective amount of a metal selected from Fe, Cu, Mn, Co, Sn, Cr, Ni, and Zn, dissolved in a polar organic solvent,
(c) sulfur compound having sulfur in the $+2$ or $+4$ oxidation state,
(d) tertiary amine,
(e) polymerization catalyst, and
(f) diluent.

The present invention also provides a method for improving the adhesion to dentin of a dental liner or primer composition comprising polymerizable phosphorus compounds, comprising the step of adding to said composition, prior to application thereof to a tooth surface, an effective amount of a metal dissolved in a polar organic solvent, said metal being selected from Fe, Cu, Mn, Co, Sn, Cr, Ni, and Zn.

Said dental bonding compositions are mixed together a short period prior to use (e.g., within 24 hours prior to use) and can be applied directly to dentin. A dental restorative, composite, or adhesive composition is then applied to the dental bonding composition-treated tooth surface, and, if desired, a dental device (e.g., an orthodontic bracket or a crown) is applied thereto. The dental restoration is completed by allowing the dental restorative, composite, or adhesive composition to harden.

Through the use of said dental bonding compositions, use of a mordant prewash step can be eliminated. Adhesion to dentin of dental restorations prepared with said dental bonding compositions is greater than adhesion to dentin of corresponding dental restorations prepared using dental liners or primers which do not contain said component (b) above.

DETAILED DESCRIPTION

Polymerizable Phosphorus Compound

In the practice of the present invention, the polymerizable phosphorus compound (viz., component (a) above) is preferably an organic ester of one or more acids of phosphorus (hereafter referred to as "phosphorus acid esters"), said ester having chlorine or bromine bonded directly to phosphorus, and the organic radical of said ester containing at least one polymerizable functional group. Said phosphorus acid esters can be characterized by the formulas (I) and (II):

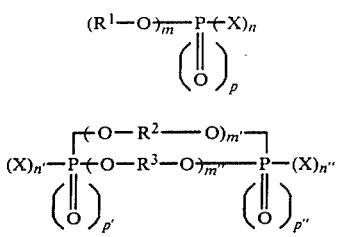

$$\begin{array}{c} (R^1-O)_{\overline{m}}-P-(X)_n \\ \| \\ (O)_p \end{array} \qquad \text{I}$$

$$\begin{array}{c} \phantom{xx}\lceil(O-R^2-O)_{m'}\rceil \\ (X)_{n'}-P-O-R^3-O)_{\overline{m''}}-P-(X)_{n''} \\ \| \phantom{xxxxxxxxxxxx} \| \\ (O)_{p'} \phantom{xxxxxxxxxx} (O)_{p''} \end{array} \qquad \text{II}$$

wherein m is 1 to 3, m' and m" are zero or 1 and are the same or different, n is 1 to 4, n' and n" are independently zero to 4 and are the same or different, with the proviso that n' and n" are both not zero, p, p', and p" are zero or 1 and are the same or different, $m+n+2p=3$ or 5, $m'+m''+n'+2p'=3$ or 5, $m'+m''+n''+2p''=3$ or 5, $R^1$ is a monovalent olefinic organic radical (preferably alkenyl, alkenoxy, cycloalkenyl, aralkenyl, or alkenaryl, having 2 to 40 carbon atoms) which can be straight chain, branched, or cyclic, can contain skeletal hetero atoms, i.e., atoms other than carbon (e.g., oxygen, sulfur, or non-basic nitrogen atoms), and can be unsubstituted or substituted with non-interfering moieties, e.g., moieties which do not interfere with free-radical polymerization of said phosphorus acid esters, $R^2$ and $R^3$ are divalent olefinic organic radicals (preferably alkenylidene, oxyalkenylidene, cycloalkenylidene, arylenealkenylidene, or alkenylidenearylene, having 2 to 40 carbon atoms) which can be straight chain, branched, or cyclic, can contain skeletal hetero atoms, can be unsubstituted or substituted with non-interfering moieties, and are the same or different, and X is Cl, Br, or $R^4$, where $R^4$ is an aliphatic or oxyaliphatic radical having 1 to 12 carbon atoms, and each X is the same as or different from other X, with the proviso that at least one X is Cl or Br.

Compounds of formula I and II contain trivalent or pentavalent phosphorus atoms. In compounds of formula I, phosphorus is bonded to at least one chlorine or bromine atom. In compounds of formula II, at least one phosphorus atom is bonded to at least one chlorine or bromine atom. Preferably phosphorus is bonded to chlorine. The preferred phosphorus acid esters desirably contain at least one double bond between phosphorus and oxygen or sulfur, with a double bond to oxygen being preferred. Most preferably two or more polymerizable functional groups per phosphorus atom are contained in the preferred phosphorus acid esters. Also, the phosphorus acid esters are preferably liquids at room temperature.

The polymerizable functional group in the preferred phosphorus acid esters is a free-radically polymerizable group, such as an olefin, and is most preferably a monofunctional or difunctional acryl or methacryl radical. Other polymerizable functional groups include monofunctional or difunctional vinyl, allyl, crotyl, and cinnamyl radicals.

Representative preferred phosphorus acid esters include:

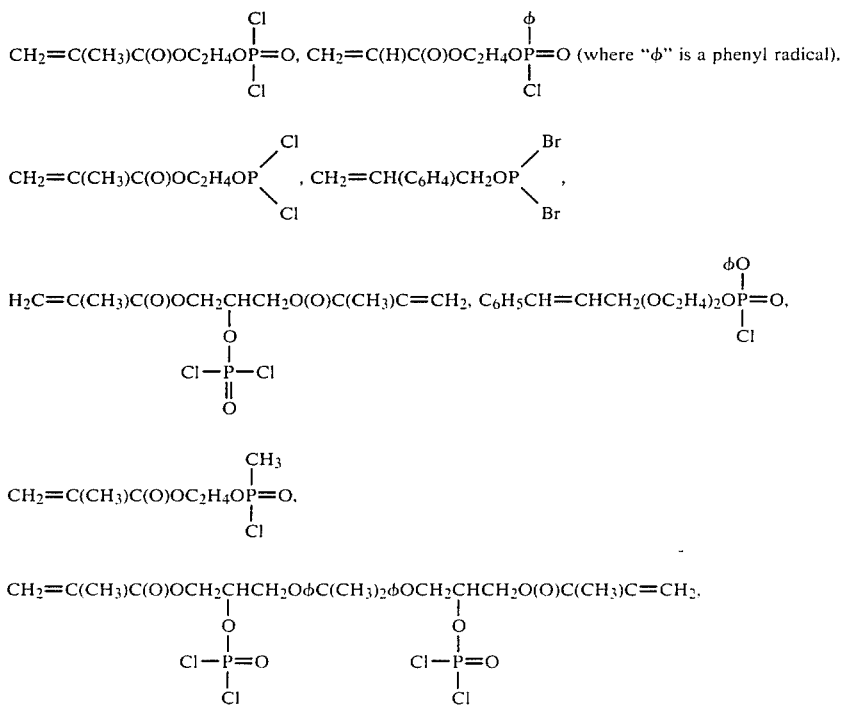

-continued

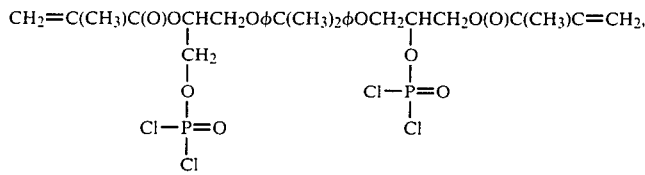

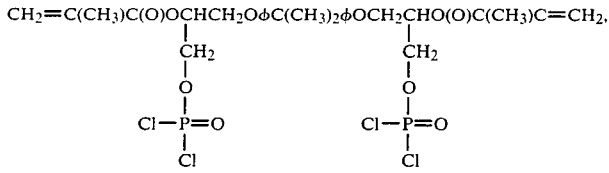

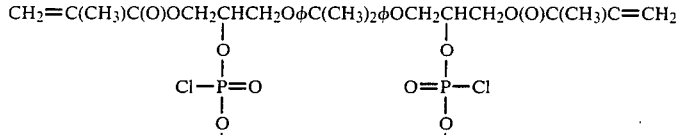

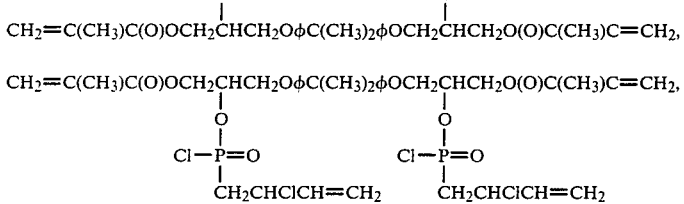

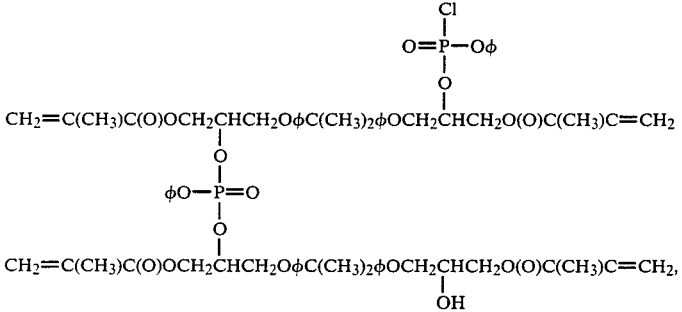

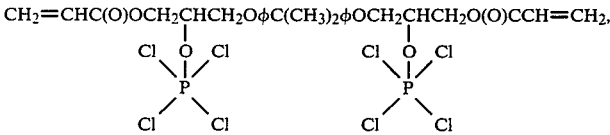

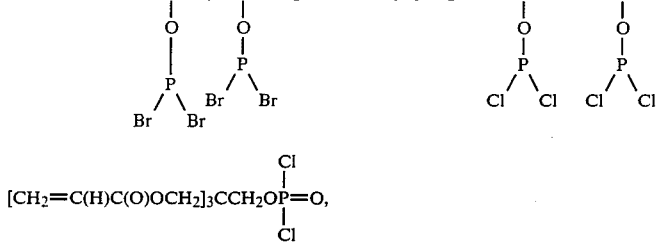

as well as mixtures of more than one of the above compounds.

The preferred phosphorus acid esters can be used individually or in the form of adducts containing more than one phosphorus acid ester. Preferably, the phosphorus acid esters are prepared by combining a chlorine- or bromine-containing phosphorus acid (e.g., phosphorus oxychloride, $POCl_3$, also known as phosphoryl chloride) with a polymerizable monomer having at least one reactive hydroxyl group (e.g., BIS-GMA and isomers thereof, sometimes referred to collectively hereafter as "BIS-GMA", such as those isomers obtained by replacement of one or both of the 2-hydroxypropylene moieties of BIS-GMA with 2-hydroxymethylethylene moieties). Such polymerizable monomers having at least one reactive hydroxyl group will be hereafter referred to as "hydroxylated monomers". When the hydroxylated monomer has a high initial viscosity, it is preferable to mix the phosphorus acid with the hydroxylated monomer and a suitable diluent (which diluent is preferably said component (f), above), e.g., triethyleneglycol dimethacrylate.

The phosphorus acid and hydroxylated monomer will react at low temperature, e.g., at room temperature, and the reaction mixture will increase in viscosity, preferably reaching an equilibrium state that is stable over time. The reaction product of such a mixture will generally be an adduct, the phosphorus acid esters of which are the product of reactions between some or all of the various hydroxyl groups of the hydroxylated monomer and available chlorine or bromine atoms of the phosphorus acid. Sufficient phosphorus acid should be added to the hydroxylated monomer to provide good bonding and handling performance in liner and primer compositions prepared therewith. For an adduct prepared by combining phosphorus oxychloride and BIS-GMA, about 0.25 to twenty percent by weight phosphorus oxychloride, and preferably about one to ten percent by weight phosphorus oxychloride should be used, based on the weight of BIS-GMA. Because BIS-GMA contains two hydroxyl groups per molecule, the above weight percentage values represent equivalent ratios of POCl$_3$ to BIS-GMA of about 0.025:1 to 1:1, preferably about 0.05:1 to 0.5:1. Suitable adjustment of such equivalent ratios should be made when the phosphorus acid esters are prepared from hydroxylated monomers having other hydroxyl functionality, e.g., monofunctionality or trifunctionality. Also, suitable adjustment of such equivalent ratios should be made when the phosphorus acid esters are prepared from phosphorus acids other than phosphorus oxychloride. Expressed in terms of the ratio of halogen atoms in the phosphorus acid to hydroxyl groups in the hydroxylated monomer, the phosphorus acid and hydroxylated monomer should be combined in a ratio of halogen atom to hydroxyl group between about 0.0375:1 to 1.5:1, preferably about 0.075:1 to 0.75:1.

If lesser amounts of phosphorus acid than those amounts sufficient to provide good bonding and handling performance are used, the resulting adduct may have low adhesion to dentin and enamel when polymerized therewith. If larger amounts of phosphorus acid than those sufficient to provide good bonding and handling are used, the resulting adduct will tend to homopolymerize, thereby having inadequate shelf life.

Other phosphorus acids which can be reacted with hydroxylated monomers to prepare the preferred phosphorus acid esters used in this invention include CH$_3$POCl$_2$, PCl$_3$, PCl$_5$, C$_6$H$_5$POCl$_2$, C$_6$H$_5$OPOCl$_2$, and PBr$_3$. Such phosphorus acids can be used singly or in combination. Phosphorus oxychloride is a preferred phosphorus acid for use in the preparation of the preferred phosphorus acid esters used in this invention.

Other hydroxylated monomers which can be used to prepare the preferred phosphorus acid esters used in this invention include hydroxyethyl methacrylate, pentaerythritol triacrylate, glycerol dimethacrylate, methyl vinyl alcohol, vinyl benzyl alcohol, allyl alcohol, crotyl alcohol, and cinnamyl alcohol.

The mixing of phosphorus acid and hydroxylated monomer can be carried out at room temperature. The attainment of equilibrium between the phosphorus acid and hydroxylated monomer can be determined by observing the viscosity of the adduct over time, with equilibrium being indicated by a leveling off of such viscosity.

Other polymerizable phosphorus compounds which can be used as said component (a) include compounds containing olefinic functionality and at least one

moiety, such as glycerophosphate dimethacrylate and the polymerizable phosphorus compounds described in U.S. Pat. Nos. 4,182,035, 4,222,780, 4,235,633, and 4,259,075, O.L.S. Nos. 2711234 and 2818068, and Japanese laid-open application Nos. 77-113089, 78-30193, 78-39331, 78-67740, 78-69494, 78-110637, 78-113843, 78-134037, 78-144939, 78-138441, 79-21438, and 79-28339. Of the polymerizable phosphorus compounds described therein, the compound

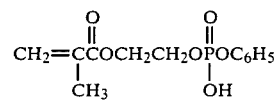

is a preferred polymerizable phosphorus compound for use in the present invention.

Metal Solution

Said solution of a metal, hereafter sometimes referred to as the "metal solution" (viz., component (b) above) enhances the adhesion of the other components of the dental bonding composition to dentin upon polymerization thereof. Metal solutions containing ions such as Fe$^{+3}$, Cu$^{+2}$, Mn$^{+2}$, and Co$^{+2}$ ions are preferred, and metal solutions containing Fe$^{+3}$ ion are most preferred. Metal solutions containing more than one metal (e.g., solutions containing Fe$^{+3}$ ion and Mn$^{+2}$ ion) can be used if desired.

The metal solution can be prepared by dissolving a salt of the desired metal in a suitable polar organic solvent. Suitable metal salts include FeCl$_3$, Fe(NO$_3$)$_3$, CuCl$_2$, Cu(NO$_3$)$_2$, CuSO$_4$, MnCl$_2$, MnF$_2$, CoCl$_2$, SnCl$_4$, CrCl$_3$, NiCl$_2$, ZnCl$_2$, hydrates thereof, and mixtures thereof. The polar organic solvent preferably is a solvent for both the metal and for the polymerizable phosphorus compound. Suitable polar organic solvents include alcohols (e.g., ethanol), ketones (e.g., acetone), polar heterocycles (e.g., tetrahydrofuran), said diluent (f), above (also described in greater detail below), and mixtures thereof. Other substances which are poor solvents for the polymerizable phosphorus compound (e.g., water) can be used as the polar organic solvent if desired, but preferably such other substances are not used or are excluded. Absolute ethanol is a preferred polar organic solvent. Other adjuvants, such as buffering agents, fungicides, dyes, pigments, indicators, and the like can also be added to the metal solution if desired.

The concentration of metal in the metal solution should be sufficient to provide an effective amount of metal in the dental bonding composition. An "effective amount", as used herein, is an amount sufficient to provide improved adhesion to dentin of dental restorations prepared with the dental bonding compositions of the invention, compared to dental restorations prepared with corresponding dental bonding compositions which do not contain said metals. An effective amount of metal in the dental bonding composition is a non-toxic amount, preferably between about $5.2 \times 10^{-5}$ and $1.9 \times 10^{-2}$ weight percent of metal based on the weight of said polymerizable phosphorus compound (a). The "concentration of metal", as used herein, is based upon the equivalent weight of elemental metal present, although, of course, a substantial portion of the metal in the metal solution may be in ionic form. The concentration of metal in the metal solution can range between trace amounts and the limit of solubility (when mixed with any other components of the metal solution) of the metal cation. Preferably, the concentration of metal in the metal solution is chosen such that mixing a given volume (e.g., one drop) of the metal solution with an equal volume(s) of solution(s) containing said components (a), (c), (d), (e), and (f) will provide the desired concentration of metal in the resulting dental bonding composition. For metal solutions containing $Fe^{+3}$ ion in ethanol, the preferred concentration of iron is between about $3.2 \times 10^{-4}$ and $1.2 \times 10^{-1}$ grams of iron per liter of ethanol, and most preferably is between about $3.2 \times 10^{-3}$ and $3.2 \times 10^{-2}$ grams of iron per liter of ethanol. Similar concentration ranges are preferred for other metals and other solvents, and range between about 2 to 700 parts per million by weight ("ppm") of metal in solvent, and most preferably between about 20 to 200 ppm.

Sulfur Compound

Said sulfur compound having sulfur in the $+2$ or $+4$ oxidation state, hereafter sometimes referred to as the "sulfur compound", (viz., component (c) above) acts as an activator for polymerization of the dental bonding compositions of this invention. "Oxidation state", as used herein, is defined according to Hendrickson et al., *Organic Chemistry*, Third Edition, pps. 796–799 (McGraw Hill Co., 1970). Suitable sulfur compounds are ordinarily alkali metal salts, such as potassium or sodium salts, or ammonium salts, of sulfur-containing anions such as sulfinate or sulfonate anions. Additional sulfur compounds which can be used in this invention include the salts of sulfurous acid having the following formulas (III), (IV), (V), and (VI):

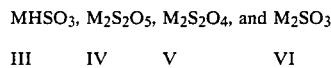

$$MHSO_3, \ M_2S_2O_5, \ M_2S_2O_4, \text{ and } M_2SO_3$$

III  IV  V  VI wherein M is a metal from Group I of the Periodic Table of the Elements, or a cation of the formula $N(R^5)_4{}^+$ where $R^5$ is a hydrogen atom, a monovalent alkyl or cycloalkyl radical having about 1 to 8 carbon atoms, or two $R^5$ taken together with the nitrogen atom to which they are joined combine to form a 5 to 7 membered ring, each $R^5$ is the same as or different from other $R^5$, and $R^5$ can contain hetero atoms which do not interfere with the functioning of the salt of sulfurous acid as an aid to polymerization of the polymerizable liquid monomer, such as oxygen, sulfur, or nitrogen. Such salts of sulfurous acid are ordinarily alkali metal salts, such as potassium or sodium salts or ammonium or alkylammonium salts, of bisulfite, metabisulfite, hydrosulfite, or sulfite anions.

Suitable sulfur compounds include $C_6H_5SO_2Na$, $CH_3C_6H_4SO_2K$, $C_6H_5SO_3Na$, $LiHSO_3$, $NaHSO_3$, $KHSO_3$, $NH_4HSO_3$, $Li_2S_2O_5$, $K_2S_2O_5$, $Na_2S_2O_5$, $(NH_4)_2S_2O_5$, $Na_2S_2O_4$, $K_2S_2O_4$, $(NH_4)_2S_2O_4$, $Li_2SO_3$, $Na_2SO_3$, $K_2SO_3$, $(NH_4)_2SO_3$, and mixtures thereof. Sodium benzene sulfinate is a preferred sulfur compound.

The amount of sulfur compound used is an amount sufficient to provide good bonding and handling performance (e.g., good shelf life and working time) in dental bonding compositions of the invention prepared therewith. A preferred amount is between about 0.5 to 10 weight percent sulfur compound based on the total weight of the dental bonding composition. The sulfur compound is preferably dissolved in a suitable solvent, such as an alcohol (e.g., ethanol), so that the desired amount of sulfur compound can be readily combined with the other components of the dental bonding composition.

Tertiary Amine

Said tertiary amine, (viz., component (d) above) acts as a polymerization accelerator for the dental bonding compositions of this invention.

Suitable tertiary amines include DHPT, N,N-dimethyl-para-toluidine, N,N-bis(2-hydroxyethyl)-3,5-xylidine, and the like. DHPT is a preferred tertiary amine.

The amount of tertiary amine used is an amount sufficient to provide good bonding and handling performance in dental bonding compositions of the invention prepared therewith. A preferred amount is between about 0.1 to 10 weight percent tertiary amine on the total weight of the dental bonding composition. The tertiary amine is preferably dissolved in a suitable solvent, such as an alcohol (e.g., ethanol), so that the desired amount of tertiary amine can be readily combined with the other components of the dental bonding composition.

Polymerization Catalyst

Said polymerization catalyst (viz., component (e) above) promotes polymerization of the dental bonding compositions of this invention.

Suitable polymerization catalysts include free-radical initiators such as peroxides, e.g., benzoyl peroxide, acetyl peroxide, lauroyl peroxide, and t-butyl hydroperoxide. Benzoyl peroxide is a preferred free-radical initiator. Photoinitiators (i.e., light-activatable catalysts) such as monoketals of aromatic 1,2-diketones or a combination of benzil and a dialkylamino acrylate or methacrylate can also be used. The amount of polymerization catalyst is an amount sufficient to provide good bonding and handling performance in dental bonding compositions of the invention prepared therewith. A preferred amount is between about 0.05 to 5 weight percent polymerization catalyst based on the total weight of the dental bonding composition. The polymerization catalyst preferably is dissolved in a suitable solvent (e.g., said diluent (f), above), and preferably is combined with said polymerizable phosphorus compound prior to shipment thereof to the user.

Diluent

Said diluent (viz., said component (f), above) serves to reduce the viscosity of the dental bonding compositions of the invention, and thereby enhance the penetration thereof into the microstructure of the tooth treatment site (e.g., into the dentin tubules). Also, the diluent preferably copolymerizes with and increases the crosslink density of the dental bonding composition, thereby increasing the hardness and strength (e.g., diametral tensile strength) thereof.

Suitable diluents include triethyleneglycol dimethacrylate (hereafter referred to as "TEGDMA"), 1,4-butanediol dimethacrylate, 1,6-hexanediol dimethacrylate, 1,8-octanediol dimethacrylate, trimethylolpropane trimethacrylate, tetraethyleneglycol dimethacrylate, neopentylglycol dimethacrylate, hydroxyethyl methacrylate, bisphenol A dimethacrylate, glycidyl methacrylate, styrene, vinyl acetate, and mixtures thereof. Preferred diluents have methacrylic functionality. TEGDMA and 1,6-hexanediol dimethacrylate are most preferred diluents.

The amount of diluent should be sufficient to lower the viscosity of the dental bonding composition to a level sufficient to provide good bonding and handling performance (e.g., ease of mixing). If the diluent is mixed with the polymerizable phosphorus compound (without addition of other components of the dental bonding composition), the viscosity of the resulting mixture preferably is between about 5 and 5000 cps at 25° C., and most preferably is less than about 3500 cps at 25° C., and the diluent preferably is between about 25 to 75 percent by volume of said mixture. Addition of solutions containing the remaining components of the dental bonding composition will typically further reduce the viscosity of the dental bonding composition below the preferred upper limits for viscosity stated above.

Other Adjuvants

The dental bonding compositions of this invention can contain other adjuvants such as surfactants, pigments, inhibitors, stabilizers against oxidation, and the like. The amounts and types of such adjuvants, and their manner of incorporation in the dental bonding compositions of this invention, will be essentially the same as currently used in existing dental liner and primer compositions familiar to those skilled in the art.

Packaging of the Dental Bonding Composition

The dental bonding compositions of the invention are preferably put up in multiple-part packages. Maximum shelf life is obtained if the metal of the metal solution is kept separate from the polymerizable phosphorus compound, the sulfur compound, and the tertiary amine until the time of use, as the metal may have a tendency to form insoluble complexes with the above-mentioned other components, thereby diminishing the bonding performance of dental restorations prefered therewith. Also, the polymerizable phosphorus compound and the sulfur compound are preferably kept separate until the time of use, as addition of the sulfur compound to the polymerizable phosphorus compound can promote homopolymerization of the latter upon standing. However, the use of multiple-part packaging for the dental bonding compositions of the invention is not a drawback, because the individual components can be readily dispensed and mixed due to their low viscosity and the small quantity of dental bonding composition typically required for a dental restoration.

For example, polymerizable phosphorus compound, polymerization catalyst, and diluent can be combined in a first part, a suitable first solvent (e.g., aqueous ethanol), sulfur compound, and tertiary amine can be combined in a second part, and a suitable second solvent (e.g., aqueous ethanol) and soluble salt of the desired metal (e.g., $FeCl_3$ or hydrate thereof) can be combined in a third part. While uncombined, the resulting three-part package will remain in a stable, uncured state. When the three parts are mixed together, e.g., by spatulation, stirring, or other means, the resulting liner composition will be ready for use.

Also, a polymerizable phosphorus compound, polymerization catalyst, and diluent can be combined in a first part, a suitable first solvent (e.g., aqueous ethanol or water) and sulfur compound can be combined in a second part, a suitable second solvent (e.g., aqueous ethanol or water) and tertiary amine can be combined in a third part, and a suitable third solvent (e.g., aqueous or absolute ethanol) and soluble salt of the desired metal can be combined in a fourth part, and the four parts later mixed together for use.

The amount of each ingredient in such multiple-part packages should be adjusted to allow sufficient working time for the practitioner to mix and apply the dental bonding composition as desired, together with attainment of the desired physical properties in the cured dental restoration.

If desired, other combinations of polymerizable phosphorus compound, desired metal, sulfur compound, tertiary amine, polymerization catalyst, diluent, and any other desired adjuvants can also be employed in multiple-part packages of dental bonding compositions of this invention. Preferably, a multiple-part dental bonding composition package offers ease of mixing, good shelf life, and desirable physical properties after cure.

In addition, where desired, one or more of said components (c)–(d) can be omitted from the dental bonding composition, provided that the omitted component(s) are present in an adjacent layer of uncured dental restorative, composite, or adhesive and can migrate into the dental bonding composition during polymerization thereof. However, this packaging method may diminish clinical reproducibility of bonding results obtained therewith.

Technique

The dental bonding compositions of the invention can be used to line prepared dentin and enamel surfaces of a dental restoration. The dental bonding compositions of the invention are applied in a manner similar to that used for existing dental liner compositions. However, cavity preparation is simplified. Excavation can be limited to the removal of damaged or defective tooth structure. Undercutting of the cavity is generally not required for retention of the restorative in the cavity. If desired, acid etching of the cavity can be omitted. This invention therefore shortens the time required for completion of a dental restoration and reduces trauma to healthy tooth structure. Following application of the dental bonding composition, the thus-treated dentin and enamel surfaces of the area to be restored can be covered with conventional restorative or composite compositions, which are hardened and finished using conventional techniques.

The dental bonding compositions of the invention can also be used as primers for the fastening of dental devices (e.g., orthodontic brackets and crowns) with dental adhesives. The dental bonding compositions of the invention are applied in a manner similar to that used for existing dental adhesive primers. However, application technique can be simplified. Satisfactory results can often be obtained in the absence of acid etching, thereby reducing damage to tooth enamel.

Where desired, e.g., to obtain very high bonding strength when dental devices are bonded to tooth enamel, acid etching of the exposed tooth enamel can be employed.

The following examples are offered to aid understanding of the present invention and are not to be construed as limiting the scope thereof.

EXAMPLE 1

Preparation of a Dental Liner Composition 10 g of phosphorus oxychloride was dissolved in a polymerizable monomer mixture (identified hereafter as "Resin A") containing 96 g BIS-GMA, 2.0 g of benzoyl peroxide, 96 g TEGDMA, 0.13 g of butylated hydroxytoluene, 0.34 g phenyl salicylate, and 0.24 g glycidyl methacrylate. The resulting mixture was allowed to stand at room temperature for 5 days. This reaction product was labeled as part "A" and was used as the first part of a three-part dental bonding composition (hereafter sometimes referred to as the "bonding agent").

A solution of 3 percent by weight sodium benzene sulfinate and 1 percent by weight DHPT in absolute ethanol was prepared. This solution was labeled as part "B" and was used as the second part of the bonding agent.

A solution containing $4.1 \times 10^{-4}$ weight percent iron in absolute ethanol was prepared using ferric chloride hexahydrate, $FeCl_3 \cdot 6H_2O$. This solution was labeled as part "C" and was used as the third part of the bonding agent.

Adhesion of the bonding agent to unetched dentin was evaluated using the following procedure. Four bovine teeth of similar age and appearance were partially embedded in circular acrylic disks. The exposed portion of each tooth was ground flat and parallel to the acrylic disk using 120 grit silicon carbide paper-backed abrasive mounted on a lapidary wheel, in order to expose the tooth dentin. During this and subsequent grinding and polishing steps, the teeth were continuously rinsed with water. Further grinding and polishing of the teeth was carried out by mounting 400 grit silicon carbide paper-backed abrasive and 600 grit silicon carbide paper-backed abrasive on the lapidary wheel.

The teeth were stored in distilled water, and dried with oil-free compressed air immediately prior to use. One drop of each part of the bonding agent was placed in a mixing tray. The drops were mixed together by hand spatulation for about 5 seconds, and the resulting mixture was then painted onto the polished tooth surface and blown into a thin film with compressed oil-free air. A conventional orthodontic bracket adhesive ("Concise 1960", commercially available from 3M) was placed on the pad surface of an orthodontic bracket (bracket no. 007 and pad no. 065, commercially available from American Orthodontics, Inc.) and the adhesive-coated bracket pad was then applied to the bonding agent-treated dentin surface. The tooth and bracket were allowed to stand for about 10 minutes at room temperature, then stored in distilled water at 37° C. for 24 hours.

Adhesion of the bonding agent to the polished, unetched bovine dentin was evaluated by placing the tooth mounting disk in a holder and clamping the holder in the jaws of an "Instron" apparatus with the layer of bonding agent parallel to the direction of pull. A loop of orthodontic wire (0.44 mm diameter) was placed around the bracket. The ends of the orthodontic wire were clamped in the pulling jaws of the Instron apparatus, thereby placing the bonding agent bond in shear stress. At a crosshead speed of 5 mm/min, the average measured shear strength of the bonding agent-dentin bond was 49.3 kg/cm$^2$.

Using the above technique, the bond strength on polished bovine enamel was also evaluated, without use of acid etching. Bond strength on unetched enamel was an average of 64.1 kg/cm$^2$.

In a comparison run, parts A and B were combined in a two-part liner composition without the use of part C. When the liner composition was evaluated using the above-described procedure, the average bond strength on unetched dentin was 38.6 kg/cm$^2$ and the average bond strength on unetched enamel was 63.3 kg/cm$^2$. This comparison run shows that use of the metal solution of Part C improved adhesion to dentin by approximately 27 percent and improved adhesion to enamel by approximately 1 percent.

In a further comparison run, an isotonic ferric chloride mordant solution containing 1.41 percent by weight $FeCl_3 \cdot 6H_2O$ was prepared and applied to polished dentin using the procedure of example 3 of U.S. Pat. No. 4,251,565, but using a 1 minute application time (instead of the thirty second application time shown therein) and with rinsing of the mordant solution from the tooth (rather than removal by suction as shown therein). Next, the above-described parts A and B (but not part C) were mixed to form a two-part liner composition. When this composition was evaluated for adhesion to dentin using the above-described technique, the average bond strength on unetched dentin was 30.1 kg/cm$^2$. This comparison run shows that use of the "mordant" prewash technique of U.S. Pat. No. 4,251,565 actually decreases adhesion to dentin when used with the two-part liner composition containing the above-described parts A and B.

In yet a further comparison run, the "mordant" prewash procedure of the preceeding paragraph was repeated, but using a prewash solution containing 20 parts per millon by weight $FeCl_3 \cdot 6H_2O$ in absolute ethanol in place of the isotonic 1.41 weight percent $FeCl_3$ solution used previously. The average bond strength on unetched dentin was 39.8 kg/cm$^2$. This further comparative example shows that an improvement in adhesion to dentin could be obtained with a prewash solution containing a very small amount of $FeCl_3$ (a much more dilute solution than that suggested in said U.S. Pat. No. 4,251,565), but the improvement in adhesion to dentin amounted to only about 0.5 percent.

EXAMPLES 2–27 AND COMPARATIVE EXAMPLES 1–3

The procedure of Example 1 was repeated, using other compositions in place of the three-part dental bonding composition containing parts A, B, and C of Example 1. Set out below in Table I are the example No., composition of each part of the dental bonding composition, and the adhesion to polished, unetched dentin and to polished, unetched enamel obtained using the dental bonding composition of each example. Also set out below are comparison examples showing the effect of omission of the metals used in this invention.

The notes following Table I show the composition of each part of the dental bonding compositions referred to therein. The notation "ppm" refers to parts per million on a weight basis.

TABLE I

| Ex. No. or Comp. Ex. No. | Dental bonding composition Part one | Part two | Part three | Bond strength on dentin, kg/cm² | Bond strength on enamel, kg/cm² |
|---|---|---|---|---|---|
| 2 | A | B | C1 | 46.2 | — |
| 3 | A | B | C2 | 44.1 | — |
| 4 | A | B | C3 | 41.4 | — |
| 5 | A | B | C4 | 30.9 | — |
| 6 | A | B | C5 | 39.1 | — |
| 7 | A | B | C6 | 41.7 | — |
| 8 | A | B | C7 | 41.1 | — |
| 9 | A | B | C8 | 49.8 | 65.2 |
| 10 | A | B | C9 | 24.6 | — |
| 11 | A | B | C10 | 39.8 | 56.0 |
| 12 | A | B | C11 | 39.2 | 66.1 |
| 13 | A | B | C12 | 47.1 | 66.1 |
| 14 | A | B1 | C13 | 47.6 | 66.1 |
| 15 | A | B2 | C13 | 45.4 | 48.2 |
| 16 | A | B3 | C13 | 63.8 | 53.2 |
| 17 | A | B4 | C13 | 40.5 | 39.8 |
| 18 | A | B5 | C13 | 56.0 | 51.7 |
| 19 | A | B6 | C13 | 65.5 | 34.2 |
| 20 | A | B7 | C13 | 65.0 | 49.8 |
| 21 | A | B8 | C13 | 58.2 | — |
| 22 | A | B8 | C14 | 57.7 | — |
| 23 | A1 | B9 | C | 51.0 | 21.3 |
| 24 | A1 | B9 | C5 | 15.1 | — |
| 25 | A1 | B9 | C6 | 26.9 | — |
| 26 | A1 | B9 | C7 | 57.6 | — |
| 27 | A1 | B9 | C8 | 25.9 | — |
| Comp. Ex. 1 | A | B8 | C15 | 42.0 | 47.3 |
| Comp. Ex. 2 | A | B10 | — | 36.4 | 54.6 |
| Comp. Ex. 3 | A1 | B9 | — | 17.0 | 32.7 |

Notes:
A is "Part A" of Example 1.
A1 is "Clearfil" catalyst resin, commercially available from Kuraray Co., Ltd., and believed to contain

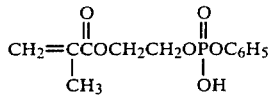

and about 2 wt. % benzoyl peroxide.
B is "Part B" of Example 1.
B1 is 3 wt. % sodium benzene sulfinate in absolute ethanol
B2 is 5 wt. % sodium bisulfite in water.
B3 is B2 plus 0.1 wt. % "Triton X-100" surfactant (commercially available from Rohm and Haas Co.).
B4 is 5 wt. % ammonium bisulfite in water.
B5 is B4 plus 0.1 wt. % "Triton X-100".
B6 is 5 wt. % sodium metabisulfite in water.
B7 is B6 plus 0.1 wt. % "Triton X-100".
B8 is 5 wt. % sodium bisulfite in 50% aqueous ethanol.
B9 is "Clearfil" universal liquid, commercially available from Kuraray Co., Ltd., and believed to contain about 3 wt. % sodium benzene sulfinate and about 1 wt. % DHPT in ethanol.
B10 is B plus 0.1 wt. % "Triton X-100".
C is "Part C" of Example 1.
C1 is 20 ppm CuCl₂ in absolute ethanol.
C2 is 20 ppm SnCl₄ in absolute ethanol.
C3 is 20 ppm MnCl₂ in absolute ethanol.
C4 is 1 ppm FeCl₃ in absolute ethanol.
C5 is 2 ppm FeCl₃ in absolute ethanol.
C6 is 5 ppm FeCl₃ in absolute ethanol.
C7 is 50 ppm FeCl₃ in absolute ethanol.
C8 is 200 ppm FeCl₃ in absolute ethanol.
C9 is 1000 ppm FeCl₃ in absolute ethanol.
C10 is 20 ppm FeCl₃ in TEGDMA.
C11 is 20 ppm FeCl₃ in a 50/50 (by volume) mixture of BIS-GMA and TEGDMA.
C12 is 200 ppm FeCl₃ in a 50/50 (by volume) mixture of BIS-GMA and TEGDMA.
C13 is 20 ppm FeCl₃ and 1.5 wt. % DHPT in absolute ethanol.
C14 is 200 ppm FeCl₃ and 1.5 wt. % DHPT in abosolute ethanol.
C15 is 1.5 wt. % DHPT in absolute ethanol.

These examples show that use of the metal solutions in dental bonding compositions of this invention provided increased adhesion to dentin and, in some cases, increased adhesion to enamel as well. These examples also show that the degree of improvement in adhesion was dependent upon the concentration of the metal solution, with adhesion values increasing, then decreasing, as the concentration of the metal solution was increased above trace concentration levels.

Various modifications and alterations of this invention will become apparent to those skilled in the art without departing from the scope and spirit of this invention, and it should be understood that this invention is not limited to the illustrative embodiments set forth herein.

What is claimed is:

1. Dental bonding compositions comprising a mixture of:
   (a) free-radically polymerizable phosphorus compound which, upon polymerization thereof, adheres to dentin and enamel,
   (b) an effective amount of an ion of a metal selected from the group consisting of Fe, Cu, Mn, Co, Sn, Cr, Ni, and Zn, dissolved in a polar organic solvent, said ion enhancing adhesion of said mixture to dentin upon polymerization of said mixture,
   (c) sulfur compound having sulfur in the +2 or +4 oxidation state, said sulfur compound acting as an activator for polymerization of said mixture,
   (d) tertiary amine,
   (e) polymerization catalyst, and
   (f) diluent.

2. Dental bonding compositions according to claim 1, wherein said polymerizable phosphorus compound comprises an organic ester of one or more acids of phosphorus, said ester has chlorine or bromine bonded directly to phosphorus, and the organic radical of said ester contains at least one free-radically polymerizable functional group.

3. Dental bonding compositions according to claim 2, wherein said organic radical is the residue remaining after removal of one or more hydroxyl hydrogen atoms from BIS-GMA or from an isomer of BIS-GMA.

4. Dental bonding compositions according to claim 3, wherein phosphorus is doubly bonded to an oxygen atom and is bonded to at least one chlorine atom, and the ratio of said phosphorus to the total amount of said BIS-GMA or isomers thereof is between 0.025:1 and 1:1.

5. Dental bonding compositions according to claim 1, wherein said polymerizable phosphorus compound has olefinic functionality and contains at least one

moiety.

6. Dental bonding compositions according to claim 1, wherein said ion is selected from the group consisting of $Fe^{+3}$, $Cu^{+2}$, $Mn^{+2}$, and $Co^{+2}$.

7. Dental bonding compositions according to claim 1, wherein said ion comprises $Fe^{+3}$ ion.

8. Dental bonding compositions according to claim 6, wherein the concentration of said ion of a metal in said dental bonding composition is between about $5.2 \times 10^{-5}$ and $1.9 \times 10^{-2}$ weight percent based upon a comparison of the equivalent weight of elemental metal to the weight of said polymerizable phosphorus compound.

9. Dental bonding compositions according to claim 6, wherein said ion comprises $Fe^{+3}$ ion and the concentration of said $Fe^{+3}$ ion in said polar organic solvent is between about $3.2 \times 10^{-4}$ and $1.2 \times 10^{-1}$ grams of iron per liter of solvent, based upon an equivalent weight of elemental iron.

10. Dental bonding compositions according to claim 9, wherein said polar organic solvent comprises ethanol and said concentration is between about $3.2 \times 10^{-3}$ and $3.2 \times 10^{-2}$ grams of iron per liter of solvent.

11. Dental bonding compositions according to claim 1, wherein said sulfur compound comprises a potassium or sodium bisulfite or arylsulfinate salt.

12. Dental bonding compositions according to claim 1, wherein said tertiary amine comprises N,N-dihydroxyethyl-p-toluidine.

13. Dental bonding compositions according to claim 1, wherein said polymerization catalyst comprises benzoyl peroxide.

14. Dental bonding compositions according to claim 1, wherein said diluent comprises triethyleneglycol dimethacrylate or 1,6-hexanediol dimethacrylate.

15. A method for improving the adhesion to dentin of a dental liner or primer composition comprising free-radically polymerizable phosphorus compounds, comprising the step of adding to said composition, prior to application thereof to a tooth surface, an effective amount of a metal compound dissolved in a polar organic solvent, said metal being selected from the group consisting of Fe, Cu, Mn, Co, Sn, Cr, Ni, and Zn.

16. A method according to claim 15, wherein said dissolved metal comprises $Fe^{+3}$.

17. A method according to claim 16, wherein said polymerizable phosphorus compound comprises an organic ester of one or more acids of phosphorus, said ester has chlorine or bromine bonded directly to phosphorus, and the organic radical of said ester contains at least one polymerizable functional group.

18. A method according to claim 16, wherein said polymerizable phosphorus compound has olefinic functionality and contains at least one

moiety.

19. Dental bonding compositions comprising a mixture of:
(a) free-radically polymerizable phosphorus compound which, upon polymerization thereof, adheres to dentin and enamel, said polymerizable phosphorus compound comprising an organic ester of one or more acids of phosphorus, said ester having chlorine or bromine bonded directly to phosphorus, the organic radical of said ester containing at least one free-radically polymerizable functional group, said organic ester having the formula

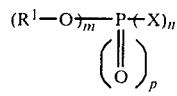

or

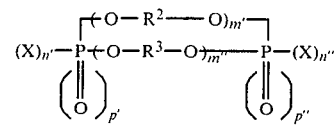

wherein
m is 1 to 3,
m' and m" are zero or 1 and are the same or different,
n is 1 to 4,
n' and n" are independently zero to 4 and are the same or different, with the proviso that n' and n" are both not zero,
p, p' and p" are zero or 1 and are the same or different,
$m+n+2p=3$ or 5,
$m'+m''+n'+2p'+3$ or 5,
$m'+m''+n''+2p''=3$ or 5,
$R^1$ is a monovalent olefinic organic radical which can be straight chain, branched, or cyclic, can contain skeletal hereto atoms, and can be unsubstituted or substituted with non-interferring moieties,
$R^2$ and $R^3$ divalent olefinic organic radicals which can be straight chain, branched, or cyclic, can contain skeletal hereto atoms, can be unsubstituted or substituted with non-interfering moieties, and are the same or different,
X is Cl, Br, or $R^4$, where $R^4$ is an aliphatic or oxyaliphatic radical having 1 to 12 carbon atoms, and each X is the same as or different from other X, with the proviso that at least one X is Cl or Br,
(b) an effective amount of an ion of a metal selected from the group consisting of Fe, Cu, Mn, Co, Sn, Cr, Ni, and Zn, dissolved in a polar organic solvent, said ion enhancing adhesion of said mixture to dentin upon polymerization of said mixture,
(c) sulfur compound having sulfur in the $+2$ or $+4$ oxidation state, said sulfur compound acting as an activator for polymerization of said mixture,
(d) tertiary amine,
(e) polymerization catalyst, and
(f) diluent.

20. Dental bonding compositions comprising a mixture of:
(a) free-radically polymerizable phosphorus compound which, upon polymerization thereof, adheres to dentin and enamel, said polyermizable phosphorus compound comprising an organic ester of one or more acids of phosphorus, said ester having chlorine or bromine bonded directly to phosphorus, the organic radical of said ester containing at least one free-radically polymerizable functional group, said organic ester having the formula

CH₂=C(CH₃)C(O)OCH₂CHCH₂OφC(CH₃)₂φOCH₂CHCH₂O(O)C(CH₃)C=CH₂,

with Cl—P=O groups (O, Cl) below each CH position

CH₂=C(CH₃)C(O)OCHCH₂OφC(CH₃)₂φOCH₂CHCH₂O(O)C(CH₃)C=CH₂,

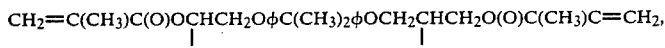

CH₂=C(CH₃)C(O)OCHCH₂φOC(CH₃)₂φOCH₂CHO(O)C(CH₃)C=CH₂, or

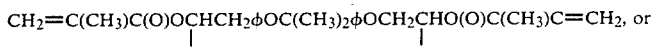

CH₂=C(CH₃)C(O)OCH₂CHCH₂OφC(CH₃)₂φOCH₂CHCH₂O(O)C(CH₃)C=CH₂

CH₂=C(CH₃)C(O)OCH₂CHCH₂OφC(CH₃)₂φOCH₂CHCH₂O(O)C(CH₃)C=CH₂,

(b) An effective amount of an ion of a metal selected from the group consisting of Fe, Cu, Mn, Co, Sn, Cr, Ni, and Zn, dissolved in a polar organic solvent, said ion enhancing adhesion of said mixture to dentin upon polymerization of said mixture, (c) sulfur compound having sulfur in the $+2$ or $+4$ oxidation state, said sulfur compound acting as an activator for polymerization of said mixture, (d) tertiary amine, (e) polymerization catalyst, and (f) diluent.

21. Dental bonding compositions according to claim 20, wherein said ion comprises $Fe^{+3}$ ion, said polar organic solvent comprises ethanol, the concentration of said $Fe^{+3}$ ion in said solvent is between about 2 and 700 ppm, said sulfur compound comprises a potassium or sodium bisulfite or arylsulfinate salt, and the concentration of said sulfur compound is between about 0.5 and 10 weight percent based on the total weight of said composition.

22. Dental bonding compositions comprising a mixture of:

(a) free-radically polymerizable phosphorus compound which, upon polymerization thereof, adheres to dentin and enamel, said polymerizable phosphorus compound having olefinic functionality, containing at least one

moiety, and comprising glycerophosphate dimethacrylate, (b) An effective amount of an ion of a metal selected from the group consisting of Fe, Cu, Mn, Co, Sn, Cr, Ni, and Zn, dissolved in a polar organic solvent, said ion enhancing adhesion of said mixture to dentin upon polymerization of said mixture, (c) sulfur compound having sulfur in the $+2$ or $+4$ oxidation state, said sulfur compound acting as an activator for polymerization of said mixture, (d) tertiary amine, (e) polymerization catalyst, and (f) diluent.

23. Dental bonding compositions comprising a mixture of:

(a) free-radically polymerizable phosphorus compound which, upon polymerization thereof, adheres to dentin and enamel, said polymerizable phosphorus compound having olefinic functionality, containing at least one

moiety, and comprising a compound of the formula

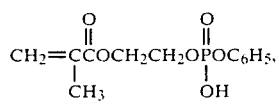

$$CH_2=C(CH_3)COCH_2CH_2OPOC_6H_5,$$ with OH on P (b) An effective amount of an ion of a metal selected from the group consisting of Fe, Cu, Mn, Co, Sn, Cr, Ni, and Zn, dissolved in a polar organic solvent, said ion enhancing adhesion of said mixture to dentin upon polymerization of said mixture, (c) sulfur compound having sulfur in the $+2$ or $+4$ oxidation state, said sulfur compound acting as an activator for polymerization of said mixture,
(d) tertiary amine,
(e) polymerization catalyst, and
(f) diluent.

24. A method for improving the adhesion to dentin of a dental liner or primer composition comprising a free-radically polymerizable phosphorus compound of the formula

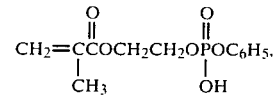

comprising the step of adding to said composition, prior to application thereof to a tooth surface, an effective amount of a metal compound dissolved in a polar organic solvent, said dissolved metal comprising $Fe^{+3}$.

* * * * *